United States Patent [19]

Judd

[11] Patent Number: 5,053,454

[45] Date of Patent: Oct. 1, 1991

[54] MULTIPLE POLYMER SYNTHESIZER

[75] Inventor: Amrit K. Judd, Belmont, Calif.

[73] Assignee: SRI International, Menlo Park, Calif.

[21] Appl. No.: 312,069

[22] Filed: Feb. 15, 1989

[51] Int. Cl.[5] .................... C08F 283/00; C08G 63/48; C08G 63/91

[52] U.S. Cl. .................................. 525/54.11; 530/333; 530/334; 422/116; 422/131; 422/134; 422/135; 435/69.1; 435/257; 435/289; 435/290; 435/317.1

[58] Field of Search ...................... 525/54.11; 530/333, 530/334; 422/116, 131, 134, 135; 435/69.1, 287, 289, 290, 317.1

[56] References Cited

U.S. PATENT DOCUMENTS

| | | | |
|---|---|---|---|
| 3,531,258 | 11/1967 | Merrifield et al. | 422/116 |
| 3,557,077 | 1/1971 | Brunfeldt et al. | 530/334 |
| 3,647,390 | 3/1972 | Kubodera et al. | 422/129 |
| 3,715,190 | 2/1973 | Park et al. | 422/100 |
| 4,065,412 | 12/1977 | Dreyer | 524/15 |
| 4,155,714 | 5/1979 | Bonner et al. | 422/116 |
| 4,353,989 | 10/1982 | Bender et al. | 435/287 |
| 4,362,699 | 12/1982 | Verlander et al. | 422/131 |
| 4,483,964 | 11/1984 | Urdea et al. | 525/54.11 |
| 4,517,338 | 3/1985 | Urdea et al. | 525/54.11 |
| 4,668,476 | 5/1987 | Bridgham | 422/62 |
| 4,671,941 | 6/1987 | Niina et al. | 422/131 |
| 4,728,502 | 3/1988 | Hamill | 422/116 |

OTHER PUBLICATIONS

Merrifield, *Science* (1986) 232:341–347.

*Primary Examiner*—Nathan M. Nutter
*Attorney, Agent, or Firm*—Irell & Manella

[57] ABSTRACT

An apparatus for simultaneously performing a multiplicity of synthesis reactions is disclosed. The synthesizer includes at least one reaction vessel having an access port and a synthesis compartment adjacent the access port. A closable exit channel with an exit port is adjacent the synthesis compartment. The apparatus also includes a base having a plurality of inlets, each of the inlets configured to receive the exit channel of the reaction vessel. A fluid outlet is present that is in communication with the plurality of inlets. A vacuum pump and vacuum line are connected to the fluid outlet for sucking excess reagents and by-products from the reaction vessel. The apparatus further includes a shaker for shaking the reaction vessel while synthesis is proceeding.

19 Claims, 2 Drawing Sheets

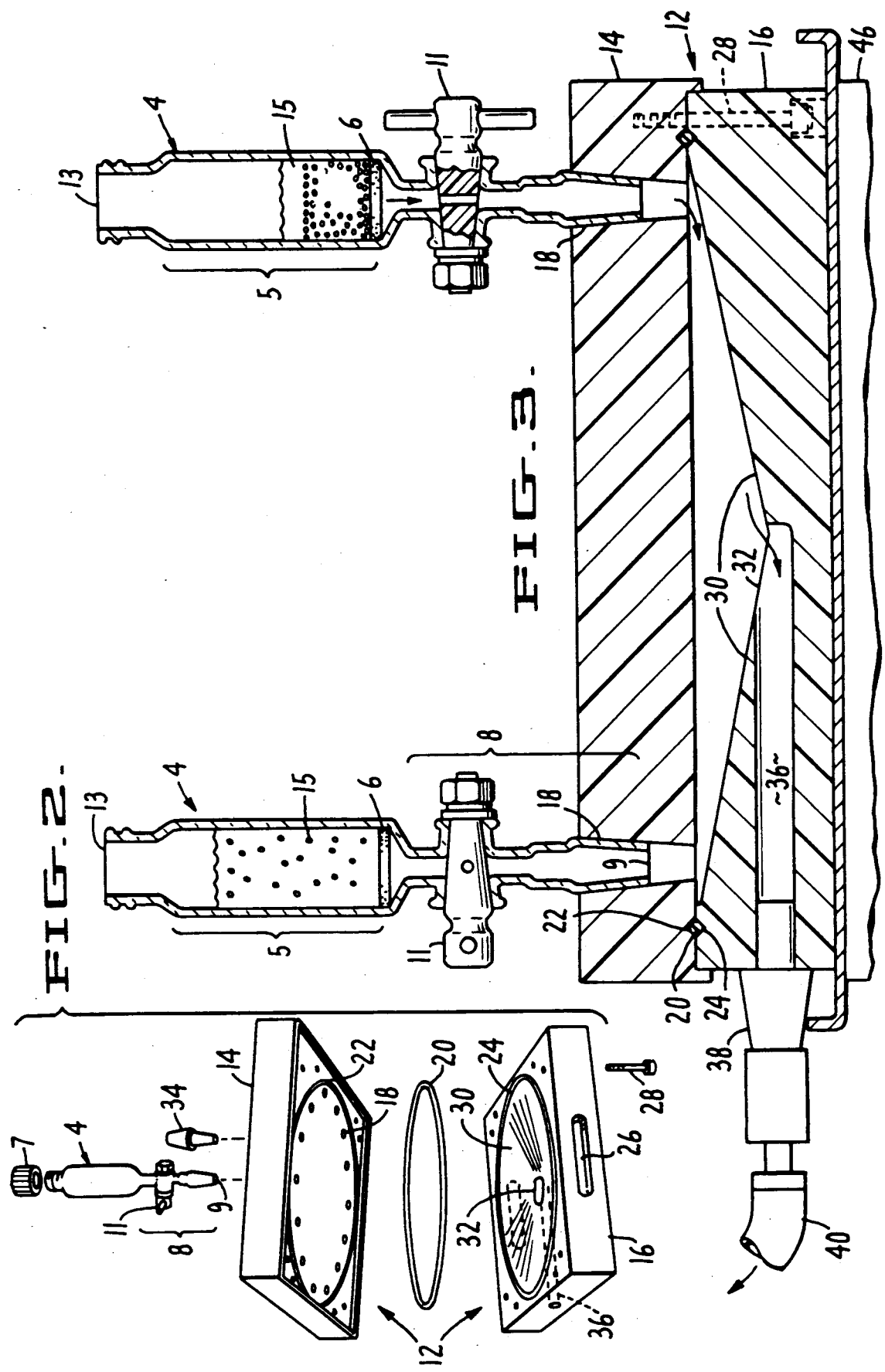

MULTIPLE POLYMER SYNTHESIZER

TECHNICAL FIELD

The present invention relates generally to solid phase synthesis apparatuses and more specifically to a multiple polymer synthesizer.

BACKGROUND OF THE INVENTION

Solid phase synthesis is commonly used to produce polymers such as peptides, polynucleotides and polysaccharides. This method of synthesis employs a technique whereby individual amino acids, mononucleotides or monosaccharides are sequentially added to a growing chain that is covalently linked to an insoluble solid support. Specifically, peptides can be produced by attaching either the amino or carboxyl group of a protected or derivatized amino acid to the solid support. The next amino acid in the desired sequence is then added under conditions suitable for forming an amide linkage. Again, the complementary amino or carboxyl group is protected prior to the addition. The protecting group is then removed from the newly added amino acid residue and the next protected amino acid added. After all the desired amino acids have been linked in the proper sequence, any remaining protecting groups are removed and the peptide cleaved from the solid support. Polynucleotides and polysaccharides can be similarly produced by the sequential addition of selectively blocked monomer units to a growing chain immobilized on the solid support.

The method is tedious and time consuming, requiring the addition of several reactants and washes. Thus, when more than one peptide is desired, the process can require days or even months.

U.S. Pat. Nos. 3,531,258 3,557,077, 3,647,390, 4,353,989, 3,362,699 and 4,668,476 all describe automated devices for solid phase peptide synthesis. Although these devices largely eliminate the need for user interaction, they are complex, costly, and only synthesize one peptide at a time. Thus, if a multiplicity of peptides are desired simultaneously, more than one machine must be used. This is often cost-prohibitive.

U.S. Pat. No. 3,715,190 discloses a manual system for solid-phase peptide synthesis. Although less costly than the automated devices, this system does not allow the simultaneous production of more than one peptide.

Apparatuses such as those disclosed in U.S. Pat. Nos. 4,728,502, 4,671,941, 4,517,338 and 4,483,964 are capable of synthesizing multiple polynucleotides simultaneously. As with those synthesizers described above, these devices are complex, automated and very costly. They also are not easily adapted for solid phase peptide synthesis.

Thus, there is a need for a simple, inexpensive system for synthesizing a multiplicity of peptides and other polymers simultaneously.

SUMMARY OF THE INVENTION

In one embodiment, the present invention comprises an apparatus for simultaneously performing a multiplicity of chemical reactions. The apparatus includes at least one reaction vessel having an access port and a synthesis compartment adjacent the access port. A closable exit channel with an exit port is adjacent the synthesis compartment. The apparatus also includes a base having a plurality of inlets, each of the inlets configured to receive the exit channel of the reaction vessel. A fluid outlet is present that is in communication with the plurality of inlets. Pressure changing means are in association with the fluid outlet for changing the pressure in the reaction vessel. The apparatus further includes shaking means for shaking the reaction vessel.

In an alternate embodiment of the instant invention, an apparatus for simultaneously performing a multiplicity of chemical reactions is disclosed. The apparatus includes at least one reaction vessel having an access port and a synthesis compartment adjacent the access port. A closable exit channel with an exit port is adjacent the synthesis compartment. Also included is a base comprising (a) an upper and lower platform, the upper platform having a plurality of inlets, each of the inlets configured to receive the exit channel of the reaction vessel, (b) guide walls defining a top surface of the lower platform, the guide walls disposed beneath the plurality inlets of the upper platform, the guide walls declined and converging to an orifice, (c) a fluid outlet disposed upon the lower platform and in communication with the plurality of inlets, and (d) a fluid channel adjacent the fluid outlet, the fluid channel disposed between the orifice and the fluid outlet. A vacuum pump is present as is a vacuum line connected to the vacuum pump and the fluid outlet. The apparatus also includes shaking means for shaking the reaction vessel.

In several preferred embodiments, the reaction vessel is elongate, circular in cross-section, includes a removable cap, and has a solid phase synthesis support disposed therein. A manually-operated stopcock serves to open and close the exit channel. A porous barrier may be present that is sufficiently dense to prevent the escape of material within the reaction vessel through the exit port except under conditions of reverse pressure.

Further embodiments of the present invention will readily occur to those of ordinary skill in the art.

BRIEF DESCRIPTION OF THE DRAWINGS

FIG. 2 is an exploded view of the preferred embodiment of the subject invention.

FIG. 3 is a cross-sectional view of the reaction vessel and base of the present invention.

DETAILED DESCRIPTION

Figure 1:
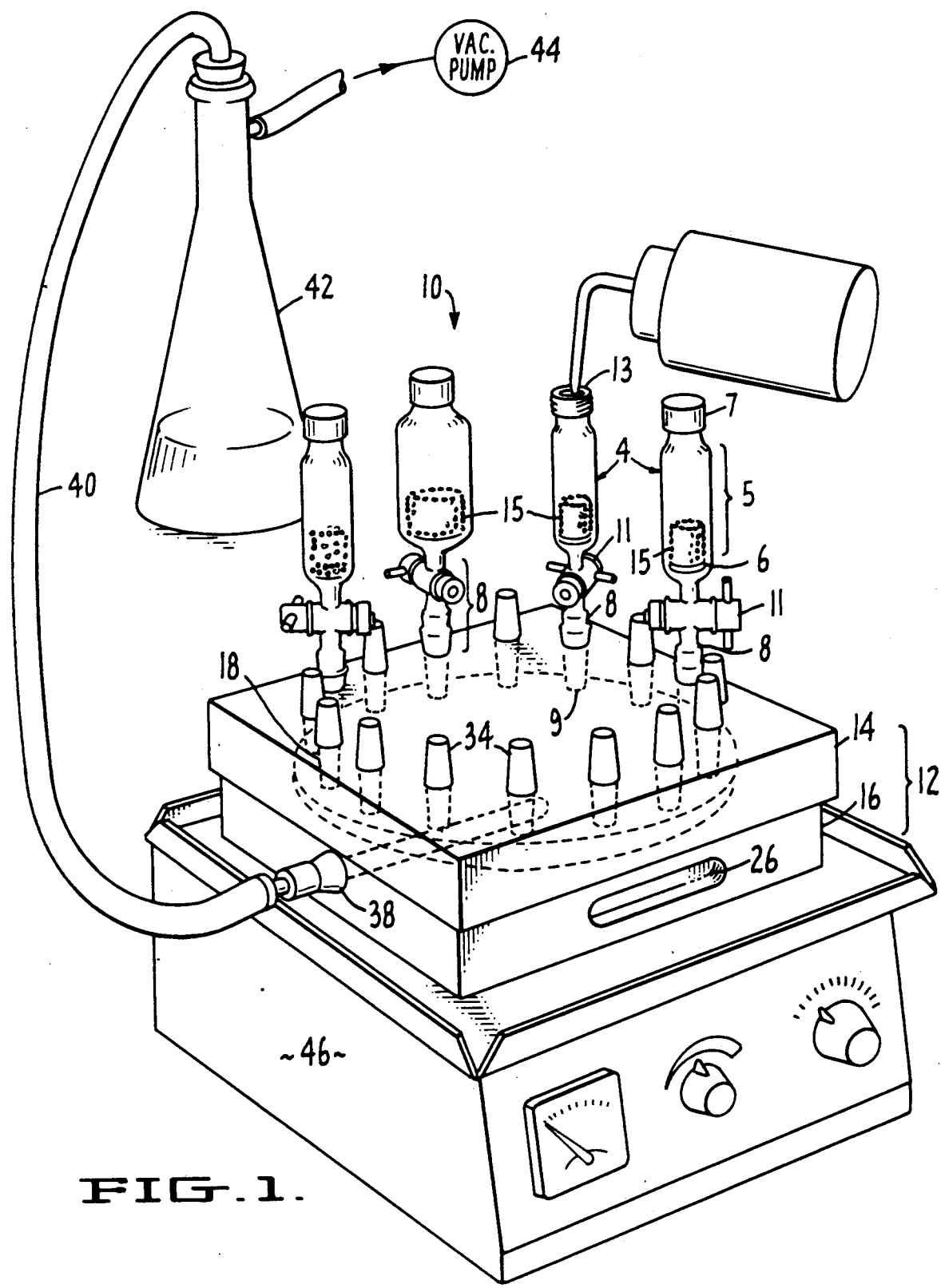
FIG. 1 is a perspective view of a multiple polymer synthesizer according to the instant invention.

Referring now to FIG. 1 of the drawings, a preferred embodiment of a multiple polymer synthesizer according to the subject invention, and generally designated by the numeral 10, can be seen. The synthesizer 10 includes a reaction vessel 4, preferably constructed of glass. Reaction vessel 4 includes an access port 13 (FIG. 3) through which reagents can be introduced. Reaction vessel 4 may also include a removable screw cap 7, a cork, plug, stopper, or any other means to prevent reactants inside from volatilizing or otherwise escaping through access port 13. Reaction vessel 4 also includes a synthesis compartment 5 adjacent the access port 13.

Reaction vessel 4 is preferably elongate in shape and circular in cross-section. Suitable dimensions and volume capacity for reaction vessel 4 will vary according to the type and size of polymer being synthesized. It has been found that for the synthesis of a peptide using 0.5–2 grams of resin, a reaction vessel with a synthesis compartment measuring approximately 6–7 cm in length, with an inner diameter of about 2–2.5 cm, and a volume capacity of approximately 20–25 ml, is particularly useful. Generally, reaction vessels used in polynucleotide synthesis will have smaller dimensions.

Synthesis compartment 5 is preferably bounded at its lower end by a porous barrier 6, sufficiently dense to prevent the escape of material present within the synthesis compartment except under conditions of reverse pressure. Porous barrier 6 can be made of glass, Teflon, porcelain, or any other material that is not reactive with the chemical reagents used during the synthesis process. Alternatively, a porous barrier need not be present so long as an alternative means of retaining the reactants within the synthesis compartment is present.

When in use, synthesis compartment 5 will contain a suitable solid phase synthesis support 15. Examples of useful supports include porous beads, gels, or resins, composed of derivatized cross-linked polystyrenes such as divinylbenzene-hydroxymethylpolystyrene copolymers, divinylbenzene-chloromethylstyrene copolymers and divinylbenzene-benzhydrylaminopolystyrene copolymers, cross-linked polyacrylamides, porous glass, silica, $\beta$-cyanoethyldiisopropyl phosphoramidite, fractosil, or other synthetic substances. The latter two are used for polynucleotide synthesis. These resins can be obtained from Applied Biosystems (Foster City, Calif.).

Adjacent synthesis compartment 5 is a closable exit channel 8. Exit channel 8 is generally smaller in diameter than synthesis compartment 5, however it need not be. Exit channel 8 terminates at exit port 9 (FIGS. 2 and 3). A multi-position valve, such as a manually-operated stopcock 11, is disposed within exit channel 8 between synthesis compartment 5 and exit port 9. Stopcock 11 can be placed in an open and closed position. When open and under conditions of reverse pressure, fluid will pass from the synthesis compartment 5, into the exit channel 8, and through the exit port 9. Alternatively, an automated multi-position valve can be used to achieve the same result.

The synthesizer 10 also includes a base 12. Base 12 is composed of Teflon, delrin or any other suitable material that does not react with the chemicals used during the synthesis process. Base 12 is preferably rectangular in configuration, however, other shapes will readily find use with the instant invention. The dimensions of base 12 will vary but preferably base 12 will be of a convenient size for standard laboratory use. Particularly useful is a base configured to fit on a conventional bench-top shaker (described below). A base with the approximate dimensions of 20-25 cm×20-25 cm×2-5 cm is so suited. During synthesis, base 12 sits on a shaker device 46 so that reagents in the reaction vessel 4 can be adequately mixed. Shaker device 46 is preferably a standard laboratory bench-top shaker such as the Orbit Shaker, available from Lab-Line.

Base 12 can be a single unit or preferably include an upper platform 14 and lower platform 16, as best illustrated in FIG. 2. An O-ring 20 is positioned within circular grooves 22 and 24 on the lower surface of the upper platform 14 and the upper surface of lower platform 16, respectively. Lower platform 16 and upper platform 14 are held together by bolts 28, screws, adhesive or any other conventional means. Lower platform 16 can include a recess 26 for receiving a user's hand to facilitate transport of the base 12.

Upper platform 14 includes a plurality of inlets 18. Each inlet 18 is configured to receive the exit channel 8 of reaction vessel 4 and secure reaction vessel 4 firmly in place upon base 12. When in use, one or more reaction vessels 4 may be placed within inlets 18. Thus, more than one polymer may be synthesized simultaneously, the number depending on the number of reaction vessels used. During synthesis, inlets not in use are blocked with inlet plugs 34.

As best illustrated in FIGS. 2 and 3, guide walls 30 define a top surface of lower platform 16. Guide walls 30 are located beneath inlets 18 and are declined and converge to an orifice 32 (FIG. 2). Thus, when stopcock 11 is in the open position and reverse pressure is applied, fluid will flow out of reaction vessel 4, through exit port 9 and through orifice 32. As seen in FIG. 3, the converging guide walls 30 also define a space beneath upper platform 14 to accommodate several milliliters of fluid and insure that liquid does not backflow into reaction vessel 4.

The synthesizer 10 also includes a fluid channel 36 (FIG. 3) adjacent the orifice 32. Fluid channel 36 terminates at fluid outlet 38. Fluid outlet 38 is connected to a vacuum line 40. A vacuum pump 44 or other suitable device, can be used to create reverse pressure and draw a vacuum in reaction vessel 4 when access port 13 is uncovered and stopcock 11 is in the open position. Thus, excess reagents and by-products can be conveniently removed from reaction vessel 4 during chemical synthesis. A waste disposal container 42 can be placed between the vacuum pump 44 and the fluid outlet 38 in the vacuum line 40. In this way, liquid waste can be easily collected for disposal. Also present is a cold dry ice trap (not shown) between the waste disposal container 42 and the pump 44.

When in use, the multiple polymer synthesizer functions in the following manner. The exit channel 8 of one or more reaction vessels 4 is placed within one or more inlets 18 of base 12. Unused inlets are plugged with inlet plugs 34. A suitable solid phase support is added to reaction vessel 4 through access port 13. Stopcock 11 is placed in the closed position and the appropriate reagent is added. The access opening 13 is covered with removable cap 7. During the reaction, reaction vessel 4 is rocked by the motion of the shaker device 46 beneath base 12. After a predetermined period of time, removable cap 7 is removed, stopcock 11 is opened and vacuum pump 44 is turned on. Fluid is sucked through the exit channel 8, out of the exit port 9, through orifice 32, fluid channel 36, and out fluid outlet 38 into vacuum line 40. Liquid flows through the vacuum line into waste disposal container 42. The appropriate reagent or wash can be added to reaction vessel 4 and the process is repeated until the desired polymer is synthesized. The resin is then recovered and the polymer cleaved from the support. Reaction vessel 4 can be soaked in an acid solution such as chromic acid, washed, and reused.

The following examples are offered for illustrative purposes only, and are not intended to limit the scope of the present invention in any way.

EXAMPLE 1

Peptide Synthesis Using the Multiple Polymer Synthesizer

Several peptides can be synthesized simultaneously using the instant multiple polymer synthesizer via the Merrifield method of peptide synthesis. See, e.g., *Solid-Phase Synthesis,* Blossey, E. C. and Neckers, D. C., eds., 1975; *Solid Phase Peptide Synthesis,* Stewart and Young, 1984; Merrifield, B. (1986) *Science* 232:341-347 and Table I below. This method involves the sequential addition of amino acids to a growing chain covalently anchored to a solid support. Specifically, commercially available tertiarybutyloxycarbonyl (Boc)-protected, C-terminal amino acid-containing support is added to each reaction vessel 4. Suitable supports can be obtained from Applied Biosystems (Foster City, Calif.). Dichloromethane (DCM) is then added, cap 7 placed over access port 13, shaker 46 is turned on, and the resin washed for approximately 5 minutes. Cap 7 is then removed, stopcock 11 opened and vacuum pump 44 turned on. After all the excess DCM has been sucked out of the reaction vessels, the DCM wash is repeated two more times.

Following the DCM washes, the deprotecting agent, trifluoroacetic acid-DCM-anisole (TFA-DCM-anisole) is added to each reaction vessel for approximately 1 and ½ minutes, removed as above and added a second time for approximately 30 minutes. Excess reagent is removed and the resin washed six times with DCM, for approximately 9 minutes/wash, as above. The resin is then neutralized by the addition of diisopropylethylamine-DCM (DIEA-DCM) for a period of approximately 1 and ½ minutes, excess reagent removed and the DIEA-DCM step is repeated. The resin is then washed six times with DCM for 9 minutes/wash as described above. The next desired Boc-protected amino acid is added to each reaction vessel in 1.0 mM DCM and allowed to react for approximately 1 and ½ minutes, excess reagent removed and the activator dicyclohexylcarbodimide (DCC) in 1.0M DCM added and allowed to remain in the vessels for approximately 2 hours. Excess reactants are removed as above and the resin washed three times with DCM as above.

The next desired Boc-protected amino acid can be added by repeating the steps above. When synthesis is complete, the resin is washed three times with EtOH, removed from the reaction vessels, and the peptides cleaved from the resin for further use. For cleavage, the peptide resin is reacted with anhydrous liquid hydrogen fluoride (HF) at 4° C. for 1 hour. After the reaction, HF is distilled off and the resin is washed with ether. The peptide is extracted into aqueous acetic acid and lyophilized to obtain a white fluffy solid.

TABLE I

Protocol for Solid Phase Peptide Synthesis

| Step | Reagent | Time (min) |
|---|---|---|
| 1 | DCM wash (3 times) | 5 |
| 2 | TFA-DCM-Indole | 1.5 |
| 3 | TFA-DCM-Indole | 30 |
| 4 | DCM wash (6 times) | 9 |
| 5 | DIEA-DCM | 1.5 |
| 6 | DIEA-DCM | 1.5 |
| 7 | DCM wash (6 times) | 9 |
| 8 | Boc-A.A. in DCM (1.0 mmoL) | 1.5 |
| 9 | DCC in DCM (1.0M) | 120 |
| 10 | DCM wash (3 times) | 5 |

It can readily be seen that the above process is time consuming, taking approximately 5 hours per amino acid residue. Thus, a peptide with 150 amino acid residues will take approximately 30 days to synthesize. The simultaneous synthesis of multiple peptides can therefore save months of time.

EXAMPLE 2

Oligonucleotide Synthesis Using the Multiple Polymer Synthesizer

Simultaneous synthesis of oligodeoxyribonucleotides can be performed using the instant synthesizer and any of several methods. Illustrative is the method described by Letsigner, R. L. and Mahadevan, V. in *J. Amer. Chem. Soc.* 88:5319–5324. Generally, this method employs the use of a cross-linked polystyrene-divinylbenzene copolymer resin. Nucleotide units can be added to a growing chain by the successive phosphorylation of the 3'-hydroxyl group with beta-cyanoethyl phosphate and dicyclohexylcarbodiimide, activation of the phosphate with mesitylenesulfonyl chloride, and condensation of the active phosphate with a nucleoside at the 5'-oxygen position. When the desired polymer has been synthesized, the resin from the reaction vessels can be removed and the oligonucleotides cleaved from the support using a basic solution. Several other methods can also be employed to synthesize oligonucleotides. See, *Solid-Phase Synthesis*, Blossey, E. C. and Neckers, D. C. eds., 1975.

EXAMPLE 3

Oligosaccharide Synthesis Using the Multiple Polymer Synthesizer

Oligosaccharides can also be synthesized using the instant invention. See, *Solid-Phase Synthesis*, Blossey, E. C. and Neckers, D. C., eds. 1975, for representative synthesis schemes. Specifically, an activated monomer unit protected by a temporary blocking group such as p-nitrobenzoate at one hydroxyl, and a persistent blocking group such as benzyl at the remaining hydroxyls, is coupled to a suitably functionalized allylic alcohol resin. The temporary blocking group is removed under mild conditions which leave the persistent blocking group attached. A simple alcoholysis reaction is then performed to attach a new monomer unit to the reactive end of the unit previously attached to the resin. Further steps include the sequential deblocking and coupling until an oligomer of the desired length is obtained. The oligomer is then cleaved from the support by oxidation and the persistent blocking groups removed from the soluble derivative.

Thus, a multiple polymer synthesizer is disclosed. Although preferred embodiments of the system have been described in some detail, it is understood that obvious variations can be made without departing from the spirit and scope of the invention as defined by the appended claims.

I claim:

1. An apparatus for simultaneously performing a multiplicity of solid phase synthesis chemical reactions, said apparatus comprising:

a plurality of reaction vessels, each of said reaction vessels having an access port, each of said reaction vessels including a synthesis compartment in communication with the access port and a closable exit channel in communication with said synthesis compartment and disposed opposite said access port with respect to said synthesis compartment, said closable exit channel with an exit port;

a base having a plurality of inlets, each of said inlets configured to receive said exit channel of one said reaction vessel;

a fluid outlet connected to said base and in communication through said base with said plurality of inlets;

pressure changing means in association with said fluid outlet for changing the pressure in said reaction vessel; and shaking means for shaking each of said reaction vessels.

2. The apparatus of claim 1 wherein said reaction vessel is substantially elongate and circular in cross-section.

3. The apparatus of claim 1 wherein said reaction vessel includes closing means for closing said access port.

4. The apparatus of claim 3 wherein said closing means comprises a removable cap for closing said access port.

5. The apparatus of claim 1 wherein each of said reaction vessels includes a multi-position valve positioned in said closable exit channel for opening and closing off said closable exit channel.

6. The apparatus of claim 5 wherein said multi-position valve comprises a stopcock.

7. The apparatus of claim 5 wherein said multi-position valve is automated.

8. The apparatus of claim 1 wherein each of said reaction vessels includes a porous barrier within said synthesis compartment between said access port and said closable exit channel, said porous barrier sufficiently dense to prevent the escape of material within each of said reaction vessels through said exit port except under conditions of reverse pressure.

9. The apparatus of claim 1 wherein said base further comprises:
- a first platform which includes said inlets;
- a second platform which includes an orifice to which each of said inlets is connected; and
- guide walls defining a surface of said second platform, said guide walls tapering toward said orifice.

10. The apparatus of claim 1 wherein said pressure changing means comprises a vacuum pump and a vacuum line connected to said vacuum pump and to said fluid outlet and positioned between said vacuum pump and said fluid outlet.

11. The apparatus of claim 10 wherein said pressure changing means further comprises a waste disposal container positioned between said vacuum pump and said fluid outlet and connected to said vacuum line.

12. An apparatus for simultaneously performing a multiplicity of solid phase synthesis chemical reactions, said apparatus comprising:
- a plurality of reaction vessels, each of said reaction vessels having an access port, each of said reaction vessels including a synthesis compartment in communication with the access port and a closable exit channel in communication with said synthesis compartment and disposed opposite said access port with respect to said synthesis compartment, said closable exit channel with an exit port;
- a base comprising (a) a first platform, said first platform having a plurality of inlets, each of said inlets configured to receive said exit channel of one said reaction vessel, (b) a second platform which includes an orifice to which each of said inlets is connected, (c) guide walls defining a surface of said second platform, said guide walls tapering toward said orifice, (d) a fluid outlet disposed upon said second platform and in communication with said plurality of inlets, and (e) a fluid channel adjacent said fluid outlet, said fluid channel disposed between said orifice and said fluid outlet;
- a vacuum pump nd a vacuum line connected to said vacuum pump and to said fluid outlet and positioned between said vacuum pump and said fluid outlet; and
- shaking means for shaking each of said reaction vessels.

13. The apparatus of claim 12 wherein said reaction vessel is substantially elongate and circular in cross-section.

14. The apparatus of claim 12 wherein said reaction vessel includes closing means for closing said access port.

15. The apparatus of claim 14 wherein said closing means is a removable cap for closing said access port.

16. The apparatus of claim 12 wherein each of said reaction vessels includes a multi-position valve positioned in said closable exit channel for opening and closing off said closable exit channel.

17. The apparatus of claim 16 wherein said multi-position valve comprises a stopcock.

18. The apparatus of claim 16 wherein said multi-position valve is automated.

19. The apparatus of claim 14 wherein each of said reaction vessels includes a porous barrier within said synthesis compartment between said access port and said closable exit channel, said porous barrier sufficiently dense to prevent the escape of material present within each of said reaction vessels through said exit port except under conditions of reverse pressure.

* * * * *